United States Patent [19]

Herwig et al.

[11] 4,062,828
[45] Dec. 13, 1977

[54] FLAME RESISTANT POLYAMIDE MOULDING COMPOSITIONS

[75] Inventors: Walter Herwig, Neuenhain, Taunus; Hans-Jerg Kleiner, Kronberg, Taunus, both of Germany

[73] Assignee: Hoechst Aktiengesellschaft, Frankfurt am Main, Germany

[21] Appl. No.: 688,895

[22] Filed: May 21, 1976

[30] Foreign Application Priority Data

May 24, 1975 Germany .............................. 2523145

[51] Int. Cl.$^2$ ............................................... C08K 5/04
[52] U.S. Cl. ............................. 260/45.7 P; 260/37 N
[58] Field of Search ..................... 260/45.7 P, 502.4 P

[56] References Cited

U.S. PATENT DOCUMENTS

| 3,157,694 | 11/1964 | Harwood | 260/502.4 P |
| 3,332,986 | 7/1967 | Block et al. | 260/502.4 P |
| 3,645,919 | 2/1972 | Kerst | 260/45.7 P X |

*Primary Examiner*—Lewis T. Jacobs
*Attorney, Agent, or Firm*—Curtis, Morris & Safford

[57] ABSTRACT

The present invention relates to novel agents for the flame-proofing of polymers, especially transparent polyamides. These agents, phosphinylphosphinic acids, are used in quantities of 3 to 40 weight percent calculated on the weight of the polymer. These flame-proofing agents can easily be prepared and render the polymers flame-proof to a high degree without deteriorating the mechanical and physical properties.

6 Claims, No Drawings

FLAME RESISTANT POLYAMIDE MOULDING COMPOSITIONS

It is known that the flammability of polymers may often be reduced by using phosphororganic compounds.

When using phosphororganic compounds for the flame-proofing of polyamides, considerable difficulties arise mainly due to the conditions of preparation and processing of the polyamides. The phosphorus containing addition compounds frequently have a too low stability at the high preparation temperatures of the polymers; they are chemically sufficiently inert only in a few cases or their physical properties such as vapor pressure, melting point, color, odor do not satisfy the requirements. When using amorphous, i.e. generally transparent polyamides there are obtained products that are no longer transparent after addition of phosphororganic compounds.

It has now been found that transparent polyamide molding compositions containing at least one of the phosphinylphosphinic acids of the formula

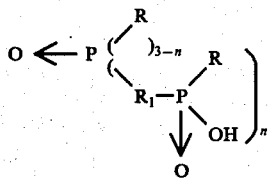

wherein R means identical or different, saturated, open chain optionally also branched or cyclic alkyl radicals having from 1 to 16 carbon atoms, aryl or aralkyl radicals having from 6 to 16 carbon atoms, $R_1$ means identical or different alkylene or arylene groups and $n$ is the integer 1, 2 or 3, have an excellent flame resistance, good mechanical and physical properties and may be prepared without difficulty in conventional experimental and industrial processes.

The invention relates to transparent polyamide molding compositions containing a flame-proofing agent, wherein the flame proofing agent is at least one of the phosphinylphosphinic acids of the formula

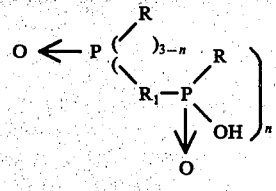

wherein
R means identical or different, saturated, open chain optionally also branched or cyclic alkyl radicals having from 1 to 16, preferably from 1 to 6 carbon atoms, aryl or aralkyl radicals having from 6 to 16 carbon atoms, especially methyl radicals,
$R_1$ means identical or different alkylene groups having from 1 to 8, preferably from 1 to 3 carbon atoms or arylene groups, preferably p- phenylene groups, especially methylene groups, and
$n$ is the integer 1, 2 or 3.

Examples of phosphorus compounds contained in the polyamide molding compositions according to the invention are those wherein R means identical or different radicals such as $CH_3$—, $C_2H_5$—, $(CH_3)_2CH$—, $C_6H_5$— and $R_1$ means —$CH_2$—, —$CH_2$—$CH_2$—, —$CH_2$—$C(CH_3)_2CH_2$—,

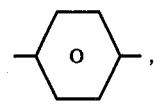

the compounds having the least carbon atoms wherein R means $CH_3$— and $R_1$ means —$CH_2$—being especially preferred.

The quantity of phosphinic acids to be used, depending on the polyamide concerned and the requirements of flameproofness, is generally in the range from 3 to 40% by weight, preferably from 5 to 30% by weight calculated on the weight of the polymer.

The phosphorus compounds contained in the polyamide moulding compositions according to the invention are obtained according to the Arbusov reaction, from

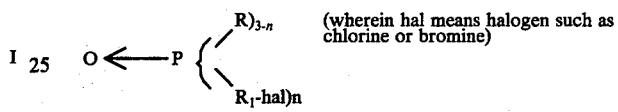

and $R-P(-O-C_mH_{2m+1})_2$ (wherein $m$ is an integer from 1 to 5) and by subsequent saponification of the esters obtained to yield the free acids. The phosphorus compounds wherein R or $R_1$ means aromatic radicals are obtained according to a variant of the Arbusov reaction developed by TAVS, which is performed in the presence of a nickel halide as catalyst.

Among suitable polyamides yielding the moulding compositions according to the invention together with the above mentioned phosphinic acids there may be mentioned preferably amorphous polyamides derived for example from 1,3- or 1,4-bis-(aminomethyl)-cyclohexane, 2,5- or 2,6-bis-(aminomethyl)-bicyclo-[2,2,1]-heptane, dimethyl-bis(4-amino-cyclohexyl)-methane, 2,2,4- or 2,4,4-trimethylhexamethylenediamine or xylylenediamine as main diamine component.

The polyamides may be derived, for example, from
$a_1$. 5 to 50% by mole, preferably 10 to 35% by mole of 1,3-bis-(aminomethyl)-cyclohexane and/or 1,4bis(aminomethyl)-cyclohexane and/or 2,5-bis-(aminomethyl)bicyclo-[2,2,1]-heptane and/or 2,6-bis(aminomethyl)bicyclo-[2,2,1]-heptane and/or at least one bis-(4-aminocyclohexyl) derivative of an alkane having from 1 to 6 carbon atoms, preferably from 1 to 3 carbon atoms, and/or m-xylylenediamine, up to 50% by mole, preferably up to 30% by mole of the m-xylyenediamine being possibly substituted by p-xylylene diamine,
$a_2$. 0 to 45% by mole, preferably 0 to 35% by mole, of at least one straight chain or branched aliphatic diamine containing from 4 to 20 carbon atoms, preferably from 6 to 12 carbon atoms, the amino groups being separated from one another by at least 4 carbon atoms, preferably by at least 6 carbon atoms,
$\beta_1$. 5 to 50% by mole, preferably 10 to 35% by mole, of at least one aromatic, especially mononuclear dicarboxylic acid having from 7 to 20 carbon atoms, preferably from 8 to 14 carbon atoms and containing carboxyl groups in meta- or para-position, $\beta_2$. 0 to 45% by mole, preferably from 0 to 35% by mole, of at least one saturated, straight chain or branched aliphatic dicarboxylic acid having from 6 to 20 carbon atoms, preferably 6 to 12 carbon atoms, the carboxyl groups being separated from one another by at least 4 carbon atoms and from $\gamma$. 0 to 80% by mole, preferably 0 to 50% by mole, of at least one aliphatic aminocarboxylic acid having from 2 to 20 carbon atoms, preferably 6 to 12 carbon atoms, especially $\omega$-amino-carboxylic acid, or their lactames, the sum of the percentages by mole of the components $(\alpha_1)$ and $(\alpha_2)$ equaling that of the components $(\beta_1)$ and $(\beta_2)$, the sum of the percentages by mole of all components $(\alpha_1)$, $(\alpha_2)$, $(\beta_1)$, $(\beta_2)$ and $(\gamma)$ being 100, the sum of the percentages by mole of the components $(\alpha_1)$ and $(\beta_1)$ being in the range of from 20 to 95, preferably from 50 to 90, the sum of the percentages by mole of the components $(\alpha_2)$, $(\beta_2)$ and $(\gamma)$ being in the range of from 5 to 80, preferably from 10 to 50 and all indications in % by mole being calculated on the sum of all components $(\alpha_1)$, $(\alpha_2)$, $(\beta_1)$, $(\beta_2)$ and $(\gamma)$.

The diamines 1,3-bis-(aminomethyl)-cyclohexane and 1,4-bis-(aminomethyl)-cyclohexane to be used for the preparation of the polyamides of the molding compositions according to the invention may be obtained by hydrogenation of the corresponding xylylenediamines. Trans-1,3-bis-(aminomethyl)-cyclohexane and mixtures of trans-1,3-bis-(aminomethyl)-cyclohexane and trans-1,4-bis-(aminomethyl)-cyclohexane are especially suitable for preparing the amorphous polyamides. The corresponding cis-diamines or mixtures of cis- and trans-diamines may also be used, however.

The diamines 2,5-bis-(aminomethyl)-bicyclo-[2,2,1]-heptane and 2,6-bis-(aminomethyl)-bicyclo[2,2,1]-heptane used for the preparation of the polyamides of the molding compositions according to the invention may be obtained in simple manner from cheap starting compounds for example as described in U.S. Pat. Nos. 2,666,748, 2,666,780 and 3,143,570. Mixtures of these diamines are preferably used, the different stereoisomeric forms of the diamines being also possibly used.

The bis-(4-aminocyclohexyl)-alkanes to be used for the preparation of the polyamides contained in the molding compositions according to the invention are prepared from cheap starting compounds, namely phenol and aldehydes or ketones, according to known methods. Bis-(4-aminocyclohexyl) derivatives of alkanes having from 1 to 6 carbon atoms, preferably from 1 to 3 carbon atoms, especially bis-(4-aminocyclohexyl)-methane and 2,2-bis-(4-aminocyclohexyl)-propane are used.

The diamines m-xylylenediamine and p-xylylenediamine to be used for the preparation of the polyamides contained in the molding compositions according to the invention may be obtained by hydrogenation of isophthalic acid dinitrile or terephthalic acid dinitrile.

Suitable straight chain or branched aliphatic diamines $(\alpha_2)$ for the preparation of the polyamides contained in the molding compositions of the invention are those having from 4 to 20 carbon atoms, preferably from 6 to 12 carbon atoms, especially hexamethylenediamine.

Further advantageous examples of aliphatic diamines $(\alpha_2)$ for the preparation of the polyamides contained in the molding compositions according to the invention are tetramethylenediamine, pentamethylenediamine, 2-methylpentamethylenediamine, 2-methylhexamethylenediamine, 3-methylhexamethylenediamine, 3,4-dimethylhexamethylenediamine, 2,2,4-trimethylhexamethylenediamine, 2,4,4-trimethylhexamethylenediamine, heptamethylenediamine, 2-methyl-4-ethylheptamethylenediamine, octamethylenediamine, nonamethylenediamine, decamethylenediamine, undecamethylenediamine and dodecamethylenediamine.

Suitable dicarboxylic acids $(\beta_1)$ for preparing the polyamides of the molding compositions according to the invention are such having from 7 to 20 carbon atoms, preferably from 8 to 14 carbon atoms. Mononuclear, dicarboxylic acids carrying carboxyl groups in meta- or para-position are expecially suitable, particularly isophthalic acid and terephthalic acid.

Further advantageous examples of aromatic dicarboxylic acids $(\beta_1)$ appropriate for the preparation of the polyamides of the molding compositions according to the invention are 2,6-pyridinedicarboxylic acid, 1,4-naphthalenedicarboxylic acid, 1,5-naphthalenedicarboxylic acid, 2,6-naphthalenedicarboxylic acid and 4,4'-diphenylsulfonedicarboxylic acid.

Mixtures of two or more aromatic dicarboxylic acids may also be used, especially mixtures of isophthalic acid and terephthalic acid.

Among suitable straight chain or branched aliphatic dicarboxylic acids $(\beta_2)$ for the preparation of the polyamides of the molding compositions of the invention there may be mentioned 2,2,4-trimethyladipic acid, 2,4,4,-trimethyladipic acid, pimelic acid, suberic acid, azelaic acid and sebacic acid.

Mixtures of two or more aliphatic dicarboxylic acids may also be used, preferably mixtures of adipic acid and decanedicarboxylic acid- 1, 10.

For preparing the polyamides of the molding compositions according to the invention there may be used as suitable aliphatic aminocarboxylic acids $(\gamma)$ those having from 2 to 20 carbon atoms, preferably 6 to 12 carbon atoms, especially $\omega$-aminocarboxylic acids. $\epsilon$-aminocaproic acid or $\omega$-aminolauric acid are preferably used.

Further advantageous examples of aliphatic aminocarboxylic acids for the preparation of the polyamides of the molding compositions according to the present invention are aminopivalic acid, $\omega$-aminoheptylic acid, $\omega$-aminocaprylic acid, $\omega$-aminopelargonic acid or $\omega$-aminoundecanoic acid.

Mixtures of two or more aliphatic aminocarboxylic acids may also be used, preferably mixtures of $\epsilon$-aminocaproic acid and $\omega$-aminolauric acid.

Instead of aminocarboxylic acids there may also be used their lactams.

The polyamides of the molding compositions according to the invention are prepared by known processes in the following manner:

Diamine(s), dicarboxylic acid(s) and optionally aminocarboxylic acid(s) or its (their) lactam(s) are introduced into a stainless steel autoclave, optionally with the addition of water. An advantageous manner frequently consists in preparing firstly a salt from the starting components, which is then introduced into the stainless steel autoclave, optionally with the addition of water. The contents of the autoclave are heated while stirring to a temperature of from about 200° to 260° C. Steam is then blown off and the temperature is increased to 265 to 300° C. Polycondensation is carried out at this temperature in a nitrogen current, optionally in vacuo, until the polyamide has attained the desired molecular weight.

Polyamides having an especially high molecular weight and good mechanical properties are obtained by submitting the polyamides prepared in an autoclave as described above to a further condensation, preferably in a double screw extruder, in vacuo.

The polyamides should have a reduced specific viscosity (RSV)-measured with a solution of 1 g of the polyamide in 100 ml of phenol/tetrachloroethane (in a weight ratio of 60:40) at a temperature of 25° C-of from 0.7 to 3.0 dl/g, preferably of from 0.9 to 2.8 dl/g.

The phosphinylphosphinic acids of the formula I may be added to the mixture for condensation in the melt as well as to the finished polyamide. They may also be added, however, at any time of the polycondensation. Their addition to the finished polyamide is advantageously performed by mixing them with the polyamide granules and by processing the mixtures obtained directly, for example in an injection molding machine or by melting them previously by heat in an extruder, granulating them and processing them after drying.

The phosphorus compounds incorporated by one of said procedures into the polyamide molding compositions are thermally stable and do not hinder the processing of the products according to the invention. A polyamide comprising for example terephthalic acid, bisaminomethylnorbornane and 33% by weight of ε-caprolactame may be admixed with 8% by weight of dimethylphosphinylmethylphosphinic acid and will it fulfill the VO specification according to the UL 94 test (Underwriters Laboratories 94). The compound is advantageously added at the beginning of the polycondensation to obtain a completely transparent, colorless condensation product which may be processed by means of conventional injection molding machines.

Besides the phosphinylphosphinic acids mineral fibrous materials may be added to the molding compositions according to the invention in usual quantities. Examples of these materials are glass fibers and fibers made from quartz, asbestos and carbon.

The thickness of the glass fibers is advantageously of from 0.2 to 50 μ, preferably from 3 to 15 μ, their length from 0.01 to 5 mm, preferably from 0.05 to 1 mm. The amount of the fibers may advantageously be as high as 50% by weight, preferably from 10 to 30% by weight, calculated on the flame-resistant polyamide molding compositions.

The polyamide molding compositions according to the invention may contain additionally known auxiliaries such as stabilizers, lubricants, dyestuffs, fillers and compounds having an antistatic effect.

The polyamide molding compositions rendered flame resistant according to the invention are suitable for the preparation of engineering parts, especially for the preparation of structural elements of electrical apparatus, mechanical transferring parts in automatic machines and structural members in computers.

The phosphinylphosphinic acids of the formula I are not only appropriate for flame-proofing transparent polyamides, but also other polyamides as well as other polymers, especially polyolefins and polystyrene.

The following examples illustrate the invention:

PREPARATION OF THE PHOSPHINYLPHOSPHINIC ACIDS

EXAMPLE 1

Preparation of the phosphinylphosphinic acid of the formula I, wherein R means $CH_3-$, $R_1$ means $-CH_2-$ and $n$ is 1.

a) Preparation of 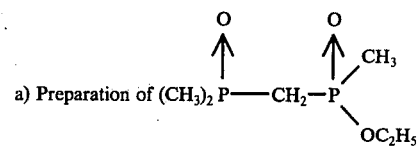

200 g of

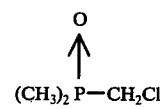

were heated to 140° C under a nitrogen atmosphere and 215 g of $CH_3P(OC_2H_5)_2$ were added dropwise for 3 hours while vigorously stirring. Ethyl chloride escaped during this process and was collected in a cold trap connected after the reaction vessel.

Thereafter the liquid obtained was distilled. 220 g of

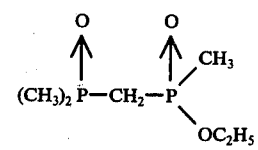

were obtained which corresponded to a yield of 70% of the theory. The boiling point was 168° C under 0.8 torr.

b) Saponification yielding 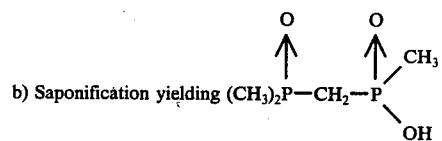

744 g of

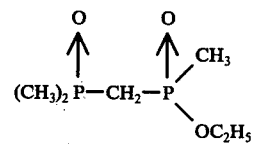

were heated to 130° C. 28 g of hydrogen chloride were introduced while vigorously stirring, whereby ethyl chloride escaped, which was collected in a cold trap connected after the reaction vessel. The reaction mixture was heated to 170° C and water was introduced dropwise while vigorously stirring, while ethanol was distilled off over a column. At the end of the reaction there was obtained 630 g of

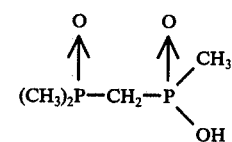

which corresponded to a yield of 99% of the theory. Melting point from 98° to 102° C.

EXAMPLE 2

Preparation of the phosphinylphosphinic acid of the formula I, wherein R means CH₃—, R₁ means —CH₂— and n is 2.

a) Preparation of

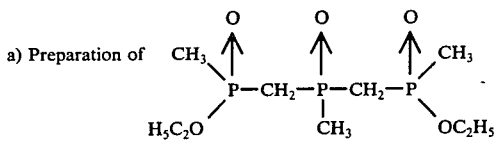

72 g of

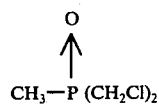

were heated to a temperature of from 120° to 130° C under a nitrogen atmosphere. 122 g of CH₃P (OC₂H₅)₂ were added dropwise while vigorously stirring, while ethyl chloride escaped, which was collected in a cold trap connected after the reaction vessel. The reaction mixture was distilled under 1 torr until a beginning decomposition could be observed. 116 g of

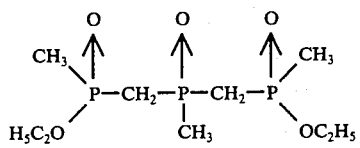

were obtained, which corresponded to a yield of 85% of the theory.

b) Saponification yielding

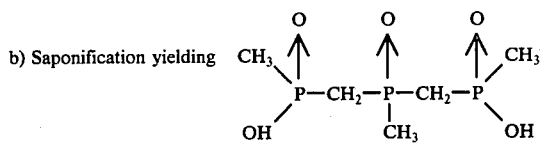

The saponification was performed in an analogous manner to Example 1 b. Yield: 95% of the theory. Melting point of the compound recrystallized from dioxane/water: 126° to 131° C.

PREPARATION OF THE POLYAMIDE MOLDING COMPOSITIONS RENDERED FLAME-RESISTANT

EXAMPLE 3a

A mixture of 66.4 g of terephthalic acid, 32.4 g of bis-amino-methylnorbornane (mixture of 2,5- and 2,6-bis-(aminomethyl)-bicyclo-[2,2,1]-heptane), 49.8 g of ε-caprolactame and 11.5 g of the phosphinylphosphinic acid prepared according to Example 1 were heated to 270° C in a round-bottomed flask in a nitrogen current while stirring mechanically, whereby the formed condensation water was slowly driven into a recipient. After about 1 and a half hours a tough, transparent and colorless condensate had rolled up round the stirrer. The product was cooled by immersion into liquid nitrogen and ground in a mill, dried in vacuo at 180° C, compressed into test specimens of 127 × 13 × 1.4 mm and submitted to a combustion test according to UL 94. The results are shown in the following table.

The bisaminomethylnorbornane mixture used as diamine component had been obtained by a known process by hydroformulation of 2-cyano-bicyclo-[2,2,1]-heptene-5 and subsequent reductive amination (reaction with ammonia and hydrogen) of the formyl compound to obtain the bis-(aminomethyl)-bicyclo-[2,2,1]-heptane mixture.

EXAMPLE 3b COMPARATIVE EXAMPLE

A polyamide was prepared as described in Example 3a, but without the addition of the phosphorus compound. The table shows the result of the combustion test.

EXAMPLE 3c COMPARATIVE EXAMPLE 24 g of decabromodiphenyl ether and 12 g of Sb₂O₃ were applied to 264 g of the polyamide used in Example 3b, in a rotating drum, and the mixture obtained was made molten in an extruder at 230° C and homogenized. The extruded cooled product was incombustible according to ASTM D 635-68, but opaque.

EXAMPLE 4

Polyamide granules (composition according to Example 3b) (RSV 1.45 dl/g) was homogenized in an extruder with 8% by weight of the phosphinylphosphinic acid obtained according to Example 1 (in a powdered form), the extruded strand was cooled in a water bath and granulated. The dried granules were examined with regard to their behaviour in a flame. The result is shown in the following table.

EXAMPLE 5a

A transparent polyamide prepared by polycondensation in the melt of 3000 g of terephthalic acid, 325 g of isophthalic acid, 2905 g of trans-1,3-bis-aminomethylcyclohexane and the quantity of AH salt (adipic acid-hexamethylenediamine salt) as obtained from 1250 g of adipic acid and 1015 g of hexamethylenediamine was homogenized in an extruder in a manner analogous to Example 4 with 7.2% by weight of the phosphinylphosphinic acid obtained according to Example 1 and examined with regard to its behaviour in a flame. The following table shows the result obtained.

EXAMPLE 5b

Example 5a was repeated but by using 6% by weight of the phosphorus compound.

EXAMPLE 5c COMPARATIVE EXAMPLE

The polyamide free from phosphorus of the Examples 5a and 5b was examined.

EXAMPLE 6

The procedure described in Example 4 was used, but using instead of the phosphinylphosphinic acid obtained according to Example 1 7.2% by weight of the phosphinylphosphinic acid obtained according to Example 2.

The examination of the product with regard to its behaviour in a flame showed VO according to UL-94.

TABLE

| Example | Polyamide components | Flame-proofing agent | % by weight | Compressed plate RSV (dl/g) | Behaviour in flame according to ASTM D 635-68 | UL 94 |
|---|---|---|---|---|---|---|
| 3 a | ta, bn ε-cl | 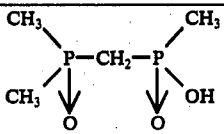 | 7.5 | 0.72 | incombustible | VO |
| 3 b+ | ta, bn, ε-cl | — | — | 1.1 | combustible | — |
| 3 c+ | ta, bn, ε-cl | decabromodiphenyl-ether/Sb$_2$O$_3$ | 9.1/4.55 | 0.72 | incombustible | — |
| 4 | ta, bn, ε-cl | 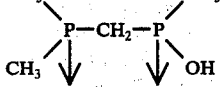 | 8.0 | 1.2 | incombustible | VO |
| 5 a | ta/ia, 1,3-bac ah salt | " | 7.2 | 0.9 | " | VO |
| 5 b | ta/ia, 1,3-bac ah salt | " | 6.0 | 0.9 | " | V2 |
| 5 c+ | ta/ia, 1,3-bac ah salt | — | — | 1.1 | combustible | — | ta = terephthalic acid, ia = isophthalic acid, bn = bisaminomethylnorbornane, 1,3-bac = 1,3-bis-aminomethylcyclohexane, ah salt = adipic acid-hexamethylenediamine-salt, ε-cl = ε-caprolactame.
RSV = red. spec. viscosity, measured with a solution of 1 g of polyamide in 100 ml of phenol/tetrachloroethane (60/40 % by weight) at 25° C.
+comparative tests

What is claimed is:

1. A flame-proofed polyamide molding composition containing as a flame-proofing substance at least one phosphinylphosphinic acid of the formula

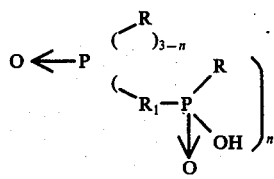

wherein
R is selected from saturated open chain-, branched and cyclic alkyl radicals having from 1 to 16 carbon atoms and aryl and aralkyl radicals having from 6 to 16 carbon atoms,
R$_1$ is selected from alkylene groups having from 1 to 8 carbon atoms and arylene groups and n is 1 to 3.

2. A polyamide molding composition as claimed in claim 1, wherein the phosphinylphosphinic acid is present in an amount of from 3 to 40% by weight, calculated on the weight of the polymer.

3. A polyamide molding composition as claimed in claim 1 wherein the polyamide is an amorphous polyamide derived from 1,3- or 1,4-bis-(aminomethyl)-cyclohexane, 2,5- or 2,6-bis-(aminomethyl)-bicyclo-[2,2,1]-heptane, dimethyl-bis-(4-amino-cyclohexyl)-methane, 2,2,4- or 2,2,4-trimethylhexamethylene-diamine or xylylene-diamine as the main diamine component.

4. A polyamide molding composition as claimed in claim 1 containing a filler.

5. A flame-proofed polyamide molding composition containing as a flame-proofing substance from 5 to 30% by weight, based on the weight of polyamide, of at least one phosphinylphosphinic acid of the formula

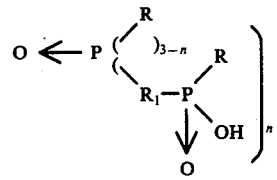

wherein R is alkyl of 1 to 6 carbon atoms, R$_1$ is methylene, and n is 1 to 3.

6. A flame-proofed transparent polyamide molding composition containing essentiall of
A. a polyamide which is a condensation product of
   a$_1$. 5 to 50 mol % of one or more diamines selected from 1,3-bis-(aminomethyl)-cyclohexane; 1,4-bis-(aminomethyl)-cyclohexane; 2,5-bis-(aminomethyl)-bicyclo-[2,2,1]-heptane; 2,6-bis-(aminomethyl)-bicyclo-[2,2,1]-heptane; bis-(4-aminocyclohexyl) derivative of an alkane having from 1 to 6 carbon atoms; and m-xylylenediamine, provided that up to 50 mol % of the m-xylylenediamine may be substituted by p-xylylene diamine,
   a$_2$. 0 to 45 mol % of one or more diamines selected from straight chain and branched aliphatic diamines containing from 4 to 20 atoms, the amino groups being separated from one another by at least 4 carbon atoms,
   b$_1$. 5 to 50 mol % of a diacid selected from aromatic dicarboxylic acids having from 7 to 20 carbon atoms and containing carboxyl groups in meta- or para-position,
   b$_2$. 0 to 45 mol % of a diacid selected from saturated, straight chain and branched aliphatic dicarboxylic acids having from 6 to 20 carbon atoms, the carboxyl groups of which are separated from one another by at least 4 carbon atoms and
   c. 0 to 80 mol % of at least one aliphatic aminocarboxylic acid having from 2 to 20 carbon atoms, on their lactams,
   the sum of the mol percentages of the components (a$_1$) and (a$_2$) equaling that of the components (b$_1$)

and (b₂), the sum of the mol percentages of all components (a₁), (a₂), (b₁), (b₂) and (c) being 100, the sum of the percentages of the components (a₁) and (b₁) being in the range of from 20 to 95, the sum of the mol percentages of the components (a₂), (b₂) and (c) being in the range of from 5 to 80, and all mol percentages being calculated on the sum of all components (a₁), (a₂), (b₁), (b₂) and (c), B. from 3% to 40% by weight, based on the weight of polyamide of at least one phosphinylphosphinic acid of the formula

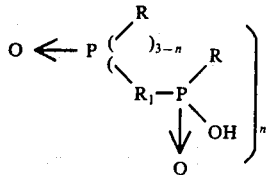

wherein
R is selected from saturated open chain, branched and cyclic alkyl radicals having from 1 to 16 carbon atoms and aryl and aralkyl radicals having from 6 to 16 carbon atoms,
R₁ is selected from alkylene groups having from 1 to 8 carbon atoms and arylene groups, and
n is 1 to 3.

* * * * *